United States Patent [19]
Himes et al.

[11] 3,956,921
[45] May 18, 1976

[54] SAMPLING DEVICE

[75] Inventors: James B. Himes, Bloomingdale; Hysam Chechakli, Des Plaines; Irvin A. Beranek, Villa Park, all of Ill.

[73] Assignee: The Richardson Company, Des Plaines, Ill.

[22] Filed: Apr. 30, 1974

[21] Appl. No.: 465,508

[52] U.S. Cl. .......................................... 73/421.5 R
[51] Int. Cl.² ......................................... G01N 1/24
[58] Field of Search ............... 73/421.5 R, 421.5 A, 73/28, 422; 23/254

[56] References Cited
UNITED STATES PATENTS

| | | | |
|---|---|---|---|
| 1,364,035 | 12/1920 | Carter | 73/421.5 R |
| 2,479,787 | 8/1949 | Stevens | 73/421.5 R |
| 2,880,615 | 4/1959 | Hardy et al. | 73/422 R |
| 3,668,825 | 6/1972 | McIlvaine | 73/28 |

*Primary Examiner*—S. Clement Swisher
*Attorney, Agent, or Firm*—Alan M. Abrams

[57] ABSTRACT

An apparatus is disclosed comprising a cooling means which can comprise an elongated coil which is connected to a reservoir means which is utilized to condense and trap material passing through the cooling means. The reservoir means is in communication with a throttling valve means which is in communication with a vacuum reservoir. The combination of elements described above can be used for sampling fluid materials and preferably, can be used for taking samples over a given period of time from a moving fluid stream such as a flue gas from a chimney or stack.

3 Claims, 1 Drawing Figure

U.S. Patent  May 18, 1976  3,956,921
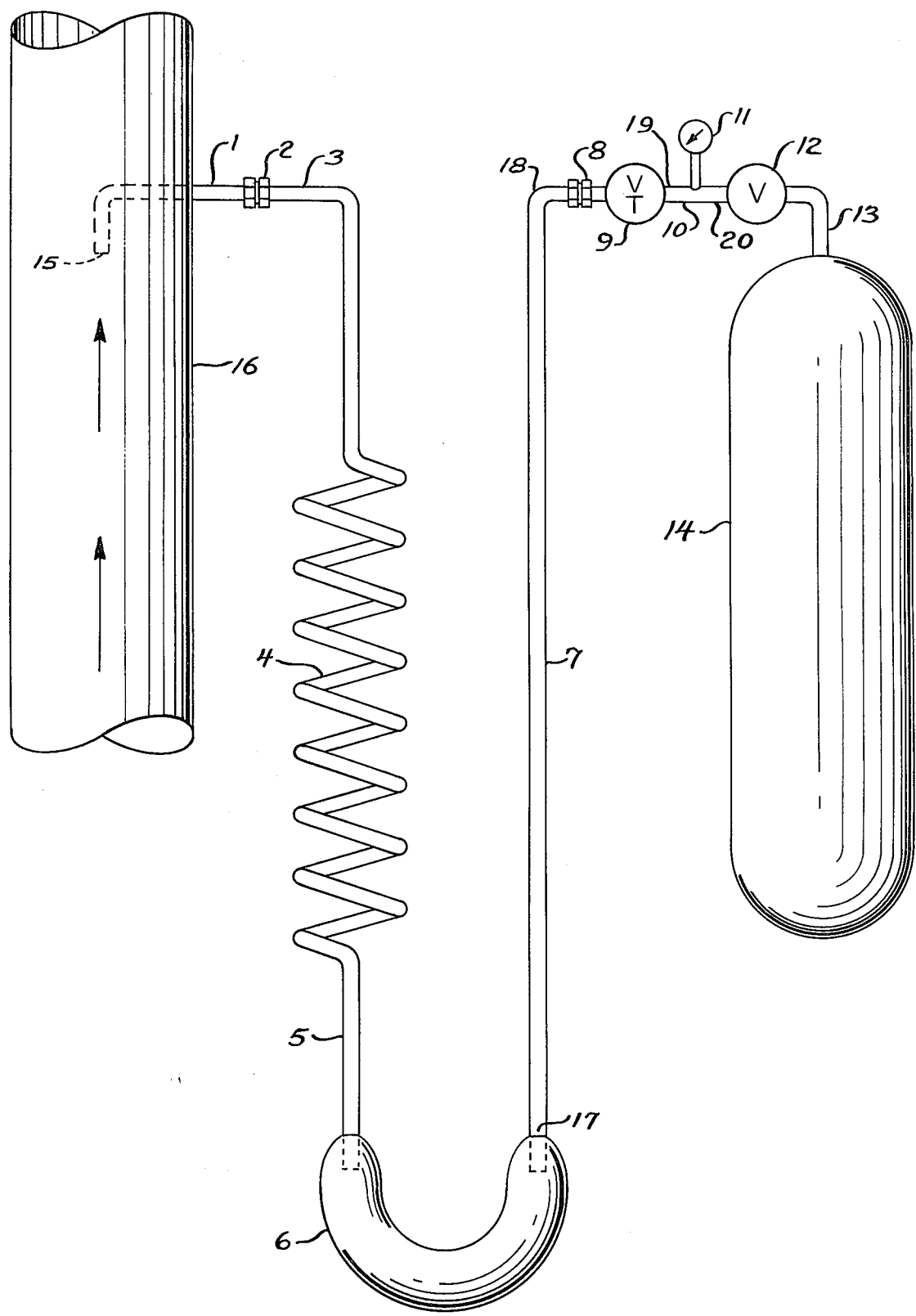

SAMPLING DEVICE

BACKGROUND OF THE INVENTION

1. Field of the Invention

The present invention relates to a sampling device which can be used to take samples from a moving stream of fluid. Such device allows the sampled fluid to be separated and retained in liquid and gaseous phases.

2. Prior Art

There are many prior art devices which can be used to sample fluids from a moving stream. In particular, vacuum bombs can be utilized to draw fluid into the evacuated bomb over a given period of time. Other devices can be utilized and can include condensers through which gases can be passed and which are maintained at a temperature, in many instances, below the dew point of the gaseous material flowing through such condenser to cause condensation. Still other devices rely on the use of an absorption medium such as a liquid or solid absorbent material to absorb the fluid or gaseous material onto the medium and thereafter through desorption of such absorbent in a vacuum the absorbed material can be released and thereafter analyzed.

Most of the prior art sampling devices, because of their design for analyzing and collecting single phase samples of a gas or a liquid, present difficulties when it is desired to sample and accurately analyze both liquid and gaseous components of a fluid stream.

The presently claimed device presents an improvement over the prior art in that it can sample a condensable fluid easily be separating the fluid into condensate (liquid) and liquid-free gaseous components. More particularly, the present device, being essentially a vacuum chamber and a condensing section, will cause gaseous material which contains condensable fluids to pass through the condensing section of the device for condensation. The liquid is trapped in the reservoir means placed below the cooling means with the non-condensable gaseous component being further passed on and into a vacuum chamber. The vacuum chamber is used to store non-condensable gaseous components of the fluid sampled. After a given amount of fluid is sampled the vacuum chamber can be sealed to hold the gaseous component of the sample fluid while the reservoir means which is adjacent to the cooling means can be sealed to hold the liquid component of the sampled fluid maintained therein. The claimed device can be separated at the connection of the reservoir and throttling valve means to provide a relatively pure gaseous non-condensable component for analysis through gas analysis means and a liquid component which can be subjected to liquid analysis.

BRIEF DESCRIPTION OF THE DRAWING

The attached drawing shows the preferred embodiment of the device claimed herein.

In particular the cooling means 4 is shown as a relatively vertically positioned helically coiled tube having an inlet 3 at the top of the tube and an outlet 5 located at the lower portion of the tube. The outlet 5 of cooling means 4 is connected to reservoir means 6 which is a chamber and acts as a liquid trap. The reservoir means 6 is connected to a vertically positioned elongated tubular means 7 having a lower end 17 and an upper end 18. The lower end 17 of the vertically positioned elongated tubular means is connected to the reservoir means 6 while the upper end o 18 vertically positioned elongated transfer means is in communication with throttling valve means 9 through optional cooling means 8.

The throttling valve means 9 is connected to the first end 19 of the horizontally positioned elongated tubular means 10. Such horizontally positioned tubular means contains pressure detecting means 11 and is connected by its second end 20 to an optional vacuum chamber valve means 12 which can be used as an additional seal between vacuum chamber 14 and the reservoir means 6. The second end 20 of the horizontally positioned elongated tubular means 10 may be connected directly to vacuum chamber 14 without the vacuum chamber valve means being used.

The inlet 3 of the cooling means is connected through optional coupling means 2 to a relatively horizontally positioned elongated sampling probe 1. Such sampling probe has an inlet portion 15 which preferably points in a downward direction when the gaseous or fluid sample to be taken is flowing in an upward direction. As shown in the drawing, the elongated and horizontally positioned sample probe 1 is passing into a flue line 16 which contains a gaseous material a portion of which can be condensable.

The upper end of the vertically positioned elongated tubular means 7 may be connected to the horizontally positioned elongated tubular means 10 through throttling valve 9 and connecting means 8. The connecting means 8 and 2 can be utilized to isolate the cooling means, the reservoir means and the vertically positioned elongated tubular means so that they may be removed from the remaining elements of the sampling apparatus and sealed off. Thereafter the liquid and gaseous portions of the sampled fluid can be separately analyzed.

DETAILED DESCRIPTION OF THE INVENTION

The device claimed herein can typically be described as containing four basic elements. Such elements generally comprise a cooling means generally represented as a helically coiled elongated tube, a reservoir means generally defined as a substantially horizontally placed tubular structure having a larger inside diameter than the inside diameter of the tubular material making up the cooling means, a throttling valve means which is in communication with said reservoir means and connects such reservoir means to the last element, the vacuum chamber. The vacuum chamber is typically a relatively large tank capable of holding a vacuum and from which the vacuum is drawn prior to the sampling device claimed herein being used.

The throttling valve means is utilized, as its name indicates, to allow the vacuum chamber to be filled with the fluid material which is being sampled over an extended predetermined period of time. In many instances the throttling valve means can comprise what is known as a throttling valve, generally a specially designed needle valve. In all cases, the throttling valve means should be a valve or other similarly designed device which can allow regulation of the amount of gas allowed to enter into the vacuum chamber.

In a preferred instance, the reservoir means 6 is connected to a vacuum chamber through two separate elements comprising a first elongated connecting tube (shown in the drawing as tube 6) which preferably is vertically placed having its lower end attached to the reservoir means and its upper end in communication or connected to the throttling valve means. The throttling valve means is then connected to the vacuum chamber through a second elongated connecting tube (shown in the drawing as tube 10) which preferably is horizontally placed and connects the throttling valve means directly to the vacuum chamber. In an even more preferred instance, the second elongated connecting tube, which is horizontally placed, contains a vacuum gauge or pressure detecting means which can be utilized to measure the amount of vacuum remaining in the vacuum chamber and allow a steady and constant flow of gaseous material to enter such vacuum chamber. In another preferred instance, the horizontally positioned second elongated connecting tube is connected to a vacuum chamber valve means which typically is any type of a valve or similarly designed device which generally operates in an open or closed position and which can be used as an additional safeguard to prevent leakage into the vacuum chamber of extraneous material prior to the taking of a sample.

The design of the vacuum chamber can include any particularly well-known and easily constructed structure. Preferably, the vacuum chamber is a vertically positioned relatively elongated tank capable of maintaining a vacuum anywhere from a few inches of mercury up to twenty-eight or more inches or mercury. In a preferred instance the vacuum chamber can have a volume anywhere from approximately three-quarters to 1 or more liters and have the vacuum chamber valve means attached to the top portion of such vacuum chamber.

The cooling means is typically elongated connecting tube vertically positioned and having a substantial portion of such tube helically positioned about a vertically positioned axis. It is preferred that the cooling means be a tube having a small inside diameter as compared to the inside diameter of the reservoir means. The reason for the difference in inside diameters is to substantially reduce the superficial gas velocity of the material passing from the cooling coils into the reservoir means in order to prevent entrapment of liquid material in the reservoir means by gaseous material passing out of the reservoir means and into the vacuum chamber.

In a preferred instance the cooling means is standard ⅛ inch tubing having wall thicknesses o approximately 0.03 inches and an inside diameter of approximately 0.065 inches.

The cooling means should be vertically positioned having an upper portion approximately 2 inches long with a bottom portion approximately the same length. Between the upper and the lower ends of such vertically positioned cooling means there can be approximately eight ¾ inch turns approximately ½ inch apart to produce the coiled ⅛ inch tube segment being approximately 4 inches long.

The reservoir means is preferably a ½ inch tube which has an inside diameter of approximately 0.44 inches with the wall thicknesses of such tube approximately 0.060 inches. Such reservoir is bent in a semicircular configuration with one of its outside walls bent around ½ inch radius. The ends of the reservoir means are preferably tapered one of which is attached by welding or other similar procedure to the cooling means comprising the standard ⅛ inch tubing. The first elongated connecting tube is vertically positioned and in a preferable instance is again a ⅛ inch standard tubing having an inside diameter of approximately 0.065 inches. It is preferable in one instance that this connecting tube be approximately 8 inches long having its lower most end attached to and in secure communication with the other end of the reservoir means. In some instances the vertically positioned first elongated connecting tube can also have a portion of its length placed in a horizontal manner in order that one end of the first elongated connecting tube can be connected directly to a throttling valve means which itself is preferably horizontally positioned.

In a preferred instance, and in order to isolate the cooling means, the reservoir means and the first elongated connecting tube from the vacuum chamber and its asssociated apparatus, it is preferable that the upper most portion of the cooling means and the upper most portion of the first elongated connecting tube, when both are vertically positioned, be connected to coupling means such as compression fittings or unions or other similar connecting devices. This will allow the separation of the cooling means, reservoir means and the first elongated connecting tube from the remaining portions of the claimed device so that the condensed material therein can be separately analyzed. Such separation can be effected through the use of such coupling means.

Such construction is, of course, preferred and will enable an analyst to separately analyze the gaseous and liquid portions of the material sampled. The gaseous material will be present in the vacuum chamber while the liquid material which has condensed will be present in the trap or reservoir means connected to the cooling means.

The throttle valve means will generally be a needle valve or any similarly designed regulating device which can be adjusted while the material being sampled enters the vacuum chamber to take a sample over a predetermined length of time and at a predetermined rate.

The optional vacuum chamber valve means may be a needle valve but preferably is a type of valve which can be used in an open or closed position. More particularly this valve is utilized to add an extra seal between the vacuum chamber and the rest of the apparatus to prevent loss of vacuum, and after the sample has been taken, to prevent loss of sampled material in the vacuum chamber.

In a preferred instance a second elongated connecting tube is horizontally positioned and is connected between the optional vacuum chamber valve means and the throttle valve means. Such second elongated connecting tube is horizontally positioned and optionally contains somewhere on it, a vacuum gauge which can be used with the throttling valve means described above to gradually fill the evacuated vacuum chamber with gaseous material.

An elongated sample probe can be attached to the inlet or upper portion of the cooling means which probe is preferably horizontally positioned and passes into a stack, conduit or pipe through which the fluid material to be sampled is passing. In a preferred instance, the elongated sample probe is a tube having approximately the same inside diameter as the cooling means of the sampling device. In one instance, the elongated sample probe is easily disconnected from the cooling means through a coupling means such as a union located on the inlet of the cooling means. In another preferred instance, the elongated sample probe is a long tube having a right angle bend at one of its ends. The right angle bend placed into the conduit through which the fluid material to be sampled is flowing and thereafter positioned so that the right angle bend is pointing in the direction opposite to the fluid flow through the conduit. In this matter it is thought that a more representative sample of the fluid to be sampled can be taken.

The coupling means connecting the elongated sample probe with the cooling means can be utilized to disconnect the elongated sample probe once the sample has been taken. Then this coupling means and the one located on the optional first elongated connecting tube can be plugged to isolate the cooling means, the reservoir and the first elongated connecting tube from the sampling probe and the vacuum chamber.

The materials of construction of all of the elements of the claimed device are preferably stainless steel or brass. Relatively erosion resistant and pressure resistant materials are preferred since, from the variety of materials sampled, corrosion resistance of the device is generally very important. In a preferable instance the entire device is made up of a non-corrosive metal such as stainless steel.

In a preferred instance, in order to effect excellent operations of the cooling means and the reservoir means (also referred to as the condensation means) and the first elongated connecting tube, the cooling means, reservoir means and first elongated connecting tube can be placed in a cooling bath or a refrigeration unit so as to allow condensation of the condensable portions of the fluid material which is being sampled. In a preferred instance the cooling means, reservoir means and first elongated connecting tube are all placed in an insulated container which contains a dry ice and acetone mixture which can be used to cool and, in most instances, condense substantially all of the condensable materials present in the fluid being sampled. When the fluid being sampled is passed through the cooling means, it comes in contact with the cool coils upon which any condensable material condenses thereafter flowing down through the coils and into the reservoir means. The non-condensable gaseous portion of the fluid being sampled passes through the cooling means, the reservoir means and up through the optional first elongated connecting tube eventually into the vacuum chamber. In such instances, when the operation of the sampling device is according to a predetermined test procedure, liquid is kept in the reservoir means and dry non-condensable gases end up in the vacuum chamber.

We claim as our invention:

1. A sampling device comprising: a condensing means comprising a coiled elongated tubular means having inlet and outlet means; said outlet means connected to a trap means comprising an elongated tubular chamber; said trap means connected to a first elongated connecting tube, which tube is connected to a throttling valve means; said throttling valve means connected to a second elongated connecting tube which second tube is connected to a vacuum chamber through a vacuum chamber valve means wherein the inside diameter of said coiled elongated tubular means is smaller than a average inside diameter of said elongated tubular chamber of said trap means.

2. Claim 1 in that said condensing means and said first elongated connecting tube means are vertically positioned.

3. Claim 2 in that said outlet of said condensing means is located below said inlet means.

* * * * *